(12) United States Patent
Siess

(10) Patent No.: US 6,942,611 B2
(45) Date of Patent: Sep. 13, 2005

(54) PARACARDIAC BLOOD PUMP

(75) Inventor: Thorsten Siess, Wuerselen (DE)

(73) Assignee: Impella CardioSystems AG (DE)

( * ) Notice: Subject to any disclaimer, the term of this patent is extended or adjusted under 35 U.S.C. 154(b) by 363 days.

(21) Appl. No.: 10/240,158

(22) PCT Filed: Mar. 27, 2001

(86) PCT No.: PCT/EP01/03467

§ 371 (c)(1),
(2), (4) Date: Sep. 27, 2002

(87) PCT Pub. No.: WO01/74419

PCT Pub. Date: Oct. 11, 2001

(65) Prior Publication Data

US 2003/0100816 A1 May 29, 2003

(30) Foreign Application Priority Data

Apr. 1, 2000 (DE) ........................................ 100 16 422

(51) Int. Cl.[7] .............................................. A61M 1/12
(52) U.S. Cl. ....................................................... 600/16
(58) Field of Search ..................................... 600/16–18

(56) References Cited

U.S. PATENT DOCUMENTS 5,824,070 A    10/1998   Jarvik

FOREIGN PATENT DOCUMENTS

| EP | 0764448 | 3/1997 |
| WO | WO 97/49439 | 12/1997 |
| WO | WO 98/43688 | 10/1998 |
| WO | WO 00/37139 | 6/2000 |

*Primary Examiner*—Scott M. Getzow
(74) *Attorney, Agent, or Firm*—Fulwider Patton Lee & Utecht, LLP

(57) ABSTRACT

The paracardiac blood pump is destined for protruding through the cardiac wall into the heart with a portion of its housing (10) and for suctioning blood from the heart. The blood is pumped into one of the blood vessels connected with the heart through a line that extends outside the heart. A cannula (30) is arranged in front of the inlet (17) of the pump ring (16). The housing (10) and the cannula (30) have approximately the same outer diameters of 13 mm at most. The housing, together with the cannula (30), can thus be inserted into the heart through a puncture hole that is produced in the cardiac wall without removing material.

8 Claims, 4 Drawing Sheets

PARACARDIAC BLOOD PUMP

Figure 1:
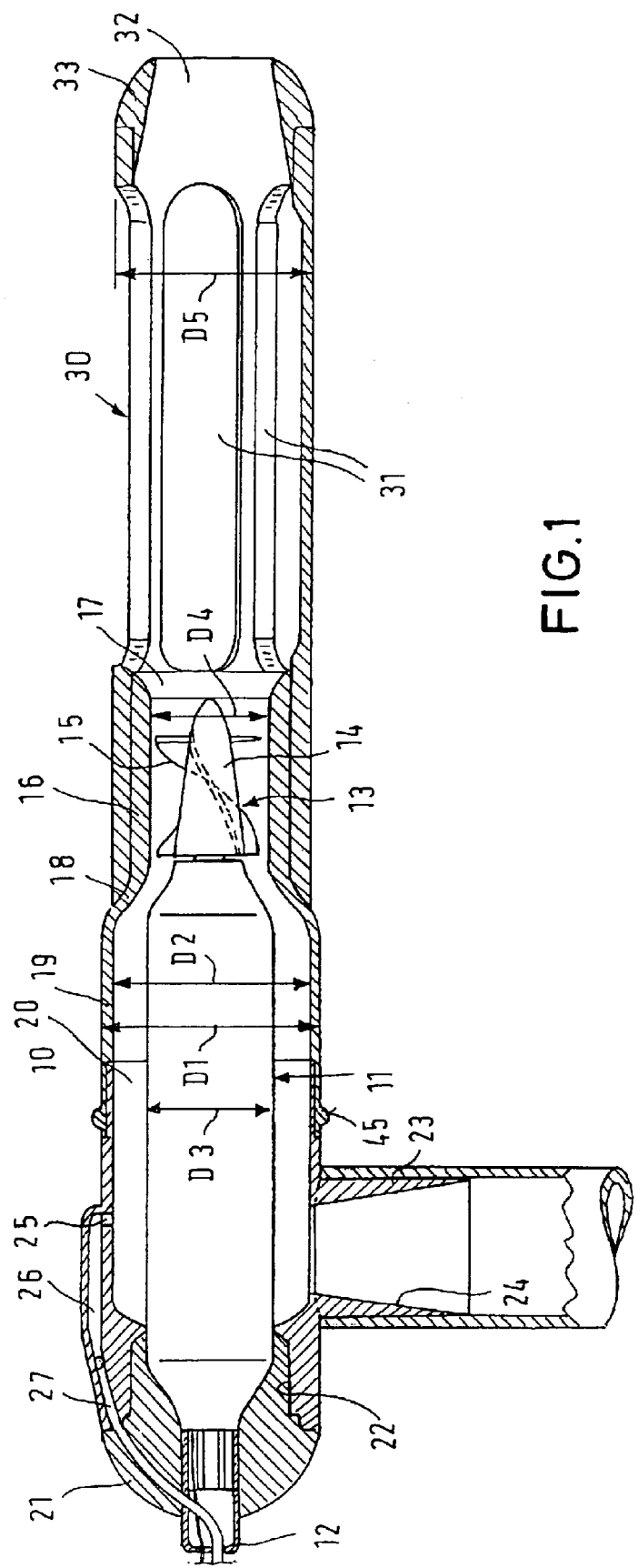

The invention relates to a paracardiac blood pump with a tubular housing wherein a drive unit for an impeller is housed in a longitudinally extending flow channel, the flow channel communicating with a laterally extending outlet tube.

A paracardiac blood pump is a blood pump pumping blood from a part of the heart and supplying it into the aorta or another target region, the housing of the blood pump being set against the heart outside, while the pump inlet has a direct connection to that ventricle from which the pumping is performed. From WO 97/49439, a thoracic blood pump is known. This blood pump comprises a tubular housing in which an electromotive drive unit is located. The drive unit is arranged in a flow channel in which blood flows around it. The blood is driven in a helical motion by an impeller arranged on the input side and circulates in the flow channel to leave the housing through a laterally branching outlet tube. As a whole, the blood pump with the housing and the outlet tube has an L-shaped configuration, whereby it is possible to put it to a port created on the cardiac wall while the outlet tube is connected with the target vessel. Such blood pumps serve for supporting the heart. They are put temporarily to the heart but are not totally inserted into the heart like intracardiac blood pumps known from WO 98/43688. With an intracardiac blood pump, no additional housing is provided wherein the drive unit is housed. The impeller rather supplies the blood flow without constricting it and without directing it in a well-defined manner.

It is the object of the present invention to provide a paracardiac blood pump which can be put to the heart from outside to support the heart without it being required to damage the cardiac wall by removing wall material.

This object is solved, according to the invention, with the features of claim 1. Accordingly, a cannula is arranged in front of the inlet of the pump ring, the outer diameter of said cannula being approximately as large as that of the housing containing the drive unit and the flow channel. The outer diameters of cannula and housing amount to 13 mm at maximum, preferably to 12 mm at maximum and particularly to 11 mm at maximum. The outer diameters of housing and cannula are approximately the same, which means that their tolerance amounts to 15% at most, particularly to 10% at most. At flow rates of about 4 to 6 liters per minute, an inner diameter of from 6 to 8 mm in the suction portion results in a flow velocity of less than 1.0 m/s. This flow velocity increases in the region of the impeller to 1.5 to 3.0 m/s and in the region of the annular flow channel, it decreases again to less than 1.0 m/s. On the one hand, in case of an appropriate flow guidance, such flow velocities are not so high that the blood would be damaged, and on the other hand, they are high enough to safely avoid, due to strong washing-out, dead water zones and thrombosis.

Since the blood pump is placed close to the heart, it can have a cannula of a relatively short length. By a short cannula, the flow losses in the region of the cannula are reduced, the pump being able to have a high hydraulic capacity, even with small dimensions.

In the region of the flow channel and the cannula, the pump has high flow velocities. These high flow velocities result in that all blood-carrying regions are washed out well, with the consequence that the danger of forming thrombi is reduced. This is important when the pump is used over a longer period of time (up to one month) because anticoagulants have to be used to a lesser degree. Thereby, the tendency to a postoperative bleeding and to a high blood loss can be significantly reduced.

The small flow cross sections, particularly in the region of the impeller, have the character of a fluid diode. This means that the reflux through the pump is little, preferably less than 1.0 l/min, even if the pump is at a standstill. It should even be possible to achieve such a little reflux in case of a cannulation from the atrium to the aorta where relatively high physiological pressures of from 80 to 100 mm Hg occur. Known comparable pumps, however, present retrograde flows of up to 3 l/min under physiological pressure conditions.

The blood pump according to the invention is configured such that it supplies the necessary output volume and, on the other hand, can be led through the cardiac wall such that the hole to be produced in the cardiac wall can be produced without removing material. The cannula and the housing can be pushed through a puncture site of the cardiac wall which then firmly surrounds the housing so that the pump supplies blood from the heart. When the pump is withdrawn, the cardiac wall closes again at the puncture site or it is clamped or sewn at this site. From the tip of the cannula to the branching outlet tube, the blood pump according to the invention is entirely cylindrical and of a small diameter so that it can be pushed through a puncture hole in the cardiac wall.

Preferably, the inner diameter of the branching outlet tube is about as large as that of the cannula. Thus about the same flow velocity as in the cannula appears in the outlet tube. The difference should be about 10% at most. High flow velocities in tube and cannula reduce the danger of thrombi formation even with low anticoagulency.

Preferably, the pump ring is configured so as to be cylindrical such that the impeller rotating therein produces an axial flow. This means that the flow in the region of the impeller is not radially deflected or only in a small measure so that the outer edges of the vanes of the impeller describe a cylindrical circumferential surface. Thereby, excessively high circumferential velocities in small gaps on the impeller are avoided, especially since the diameter of the pump ring and that of the impeller can be manufactured precisely and an axial attachment of the impeller does not effect a change of the gap.

According to a suitable embodiment of the invention, a pressure sensor for measuring the pressure of the blood to be pumped is provided on the housing. The signal of the pressure sensor is evaluated for detecting different operating states and/or detecting the current volume flow rate. It has been found out that a single pressure sensor is sufficient to detect the current volume flow rate. The respective pressure is unambiguously related to the flow rate. This relation can be detected by gauging. Moreover, extraordinary operating states, such as an obstruction of the blood flow on the outlet side or of the blood flow on the inlet side, can be detected by measuring the pressure.

Hereinafter, an embodiment of the invention is explained in detail with respect to the drawings.

Figure 2:
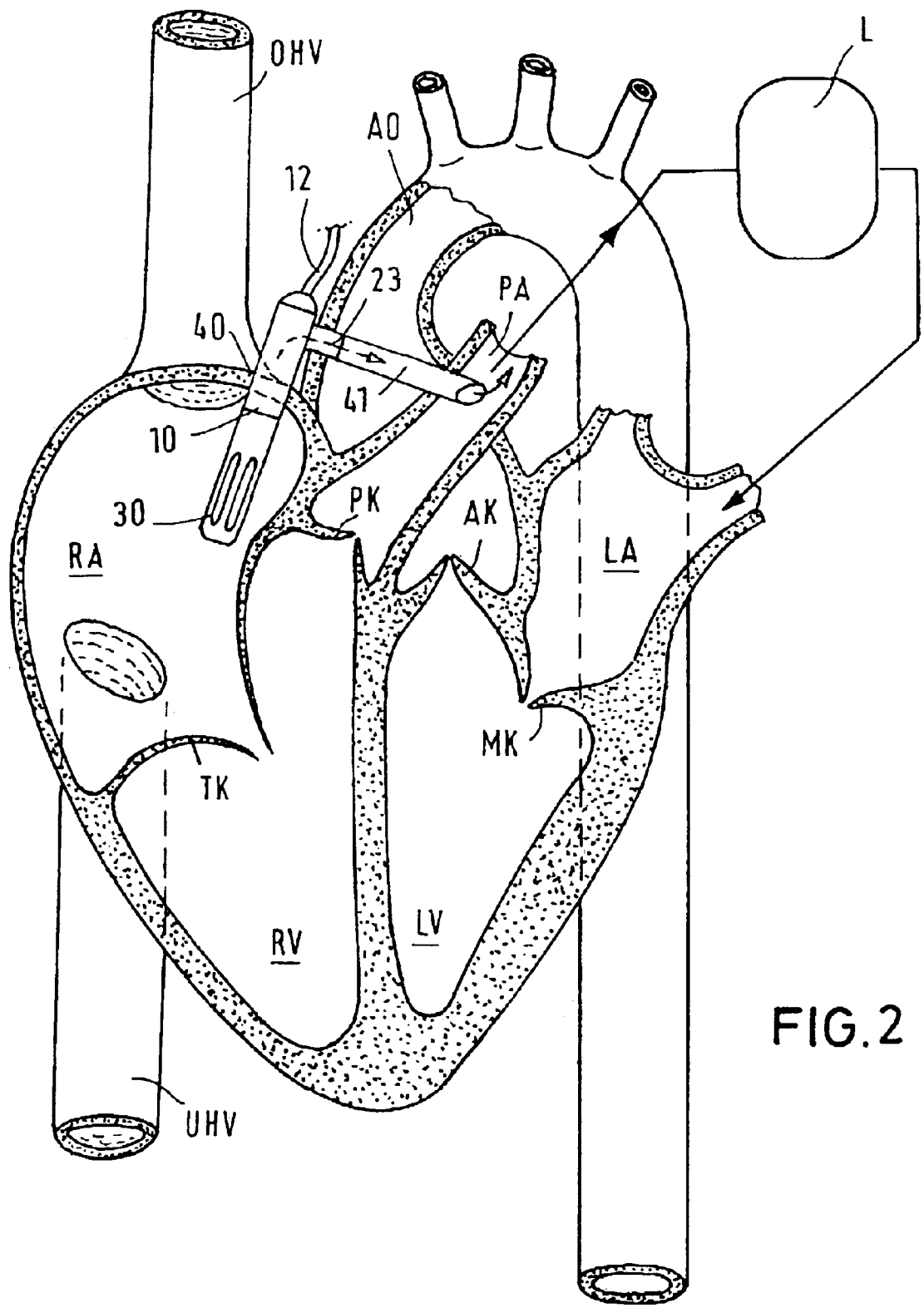
Figure 3:
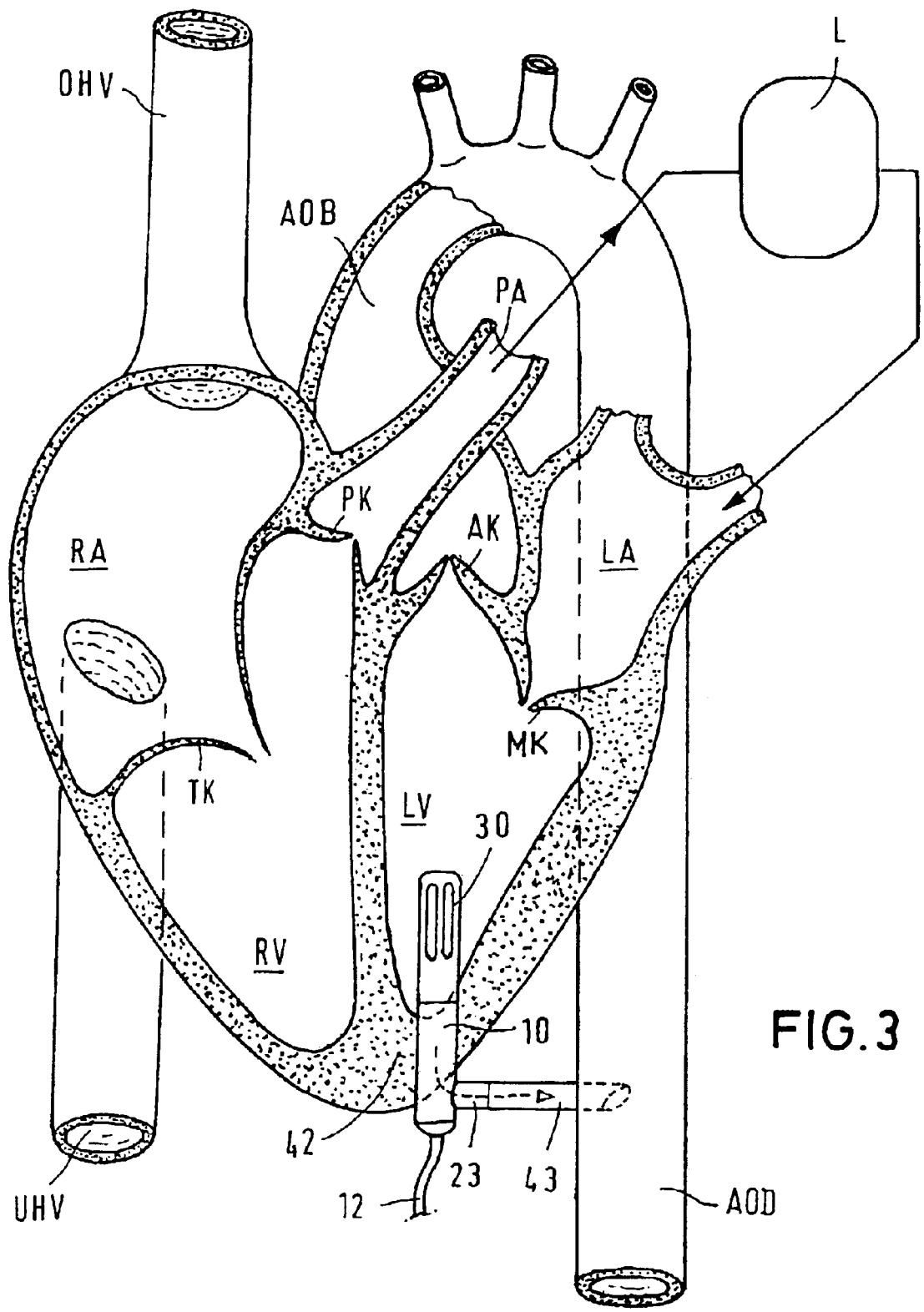
Figure 4:
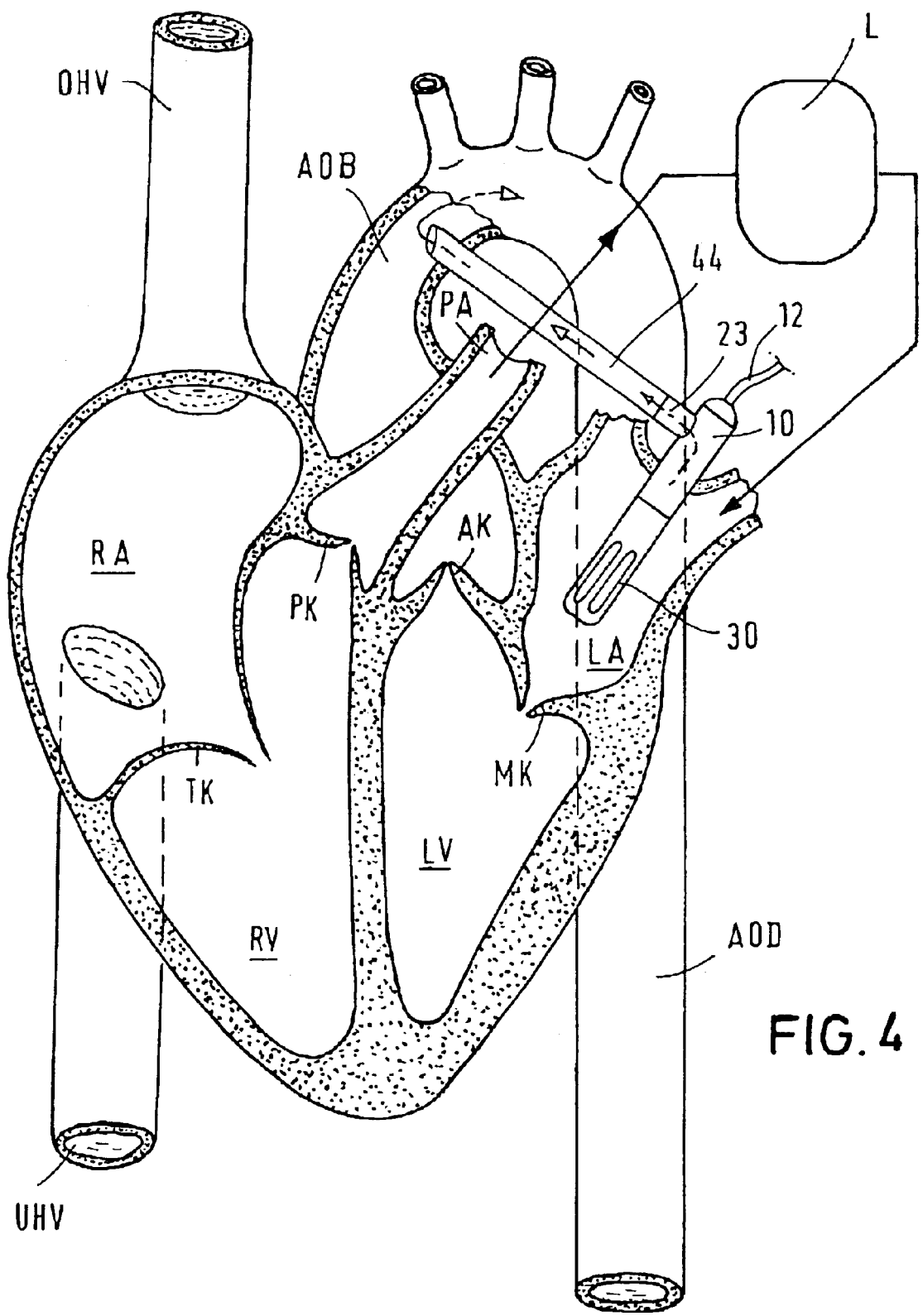

In the Figures:

FIG. 1 shows a longitudinal section through the paracardiac blood pump according to the invention, FIG. 2 shows an atrial implantation of the blood pump for the right heart support, FIG. 3 shows an apecal implantation of the blood pump for the left heart support, and FIG. 4 shows an atrial implantation of the blood pump for the left heart support.

The blood pump illustrated in FIG. 1 has a longitudinal, substantially cylindrical housing 10 in which the drive unit 11 is coaxially arranged. The drive unit 11 includes an electric motor (not illustrated). Via electrical lines passing through a catheter 12 connected with the rear housing end, it is connected with an electric control and supply unit. The impeller 13 is seated on a shaft of the drive unit 11, said impeller comprising a hub 14 conically enlarging from the front end and vanes 15 projecting therefrom and extending helically around the hub 14. The edges of the vanes 15 move on a cylindrical surface forming the envelope of the impeller 13.

The impeller 13 rotates in a cylindrical pump ring 16 the diameter of which is about the same as that of the envelope of the impeller. The running gap amounts to about 0.1 mm. This represents a good compromise between blood damage and hydraulic losses. At its front end, the pump ring 16 has an axial inlet 17 consisting here of a peripheral input bevel. The rear end of the pump ring 16 is followed by vane- and rotor-free transition region 18 wherein the diameter continuously enlarges from that of the pump ring to that of the housing portion 19 surrounding the drive unit 11. An annular flow channel 20 is formed between the wall of the housing portion 19 and the outer surface of the pump unit 11.

At the rear end of the housing 10, a holding body 21 consisting of hardened adhesive is located which fills out a recess 22 of the housing and forms a rounded projection protruding backwards and holding the rear end of the drive unit 11. The drive unit 11 thus projects from the holding body 21 in the manner of a cantilevered beam, without any lateral support.

Near the rear end of the flow channel 20, an outlet tube 23 laterally branches from the pump housing. This outlet tube 23 extends tangentially to the flow channel 20. In flow direction, its inner surface 24 enlarges in the way of a diffuser with a cone angle of 8° at most to avoid flow interruptions. A hose with even and smooth transition can be connected to the outlet tube 23.

In the region of the flow channel 20, a pressure detection opening 25 communicating with the flow channel 20 is provided on the housing wall. From the pressure detection opening 25, a pressure channel 26 leads into the lumen of a hose 27 extending through the catheter 12. At the proximal end of the catheter, a pressure sensor can be connected to detect the pressure at the place of the pressure detection opening 25. As an alternative, a pressure sensor can be installed at the pressure detection opening 25.

Alternatively, the pressure detection opening can be arranged, with axial orientation, on the rear end wall in immediate proximity of the holding body 21 or, with radial orientation, on the pump ring 16 in the region of the impeller 13.

The pressure prevailing in the flow channel 20 gives information about the current volume flow and also about particular operational conditions, such as, for example, an occlusion at the pump inlet or at the outlet. The monitoring of these parameters is effected by a single absolute value measuring of the pressure, i.e., without a differential pressure measuring.

A tubular cannula 30 mounted on the pump ring 16 extends from the housing 10. The cannula 30 has longitudinally extending slots 31 arranged so as to be peripherally distributed, and an axial opening 32 in a rounded cap 33 at the front end. The length of the cannula 30 does not exceed the length of the housing 10, the pump ring 16 belonging to the housing.

In the described embodiment, the outer diameter D1 of the housing portion 19 is 11 mm. The inner diameter D2 in the region of the flow channel 20 amounts to 10 mm. The drive unit 11 has a diameter D3 of <7.0 mm. The inner diameter D4 of the pump ring 16 amounts to 6 mm. The outer diameter D5 of the cannula 30 amounts to 10 mm and the inner diameter of the cannula amounts to 8 mm.

The mentioned dimensions result in blood flow rates of from 1.5 to 3 m/s in the region of the pump ring, from 1.0 to 1.5 m/s in the region of the flow channel 20, and of 0.5 m/s in the region of the outlet tube 23. The drive unit 11 runs at a high rotational speed of from 25,000 to 30,000 rpm. In doing so, the impeller 13 delivers 4 to 6 l (liters) of blood per minute under physiological pressure conditions.

The entire housing 10 including the pump ring 16 has a length of about 50 mm, and the portion of the cannula 30 projecting beyond the pump ring has a length of about 35 mm.

Through a puncture hole in the cardiac wall, the paracardiac blood pump is introduced into the heart in such a manner that the housing 10 sealingly closes the puncture hole while the cannula 30 is in the interior of the heart and the outlet tube 23 outside the heart. The puncture hole in the cardiac wall has been made without removing cardiac wall tissue. This facilitates the closing of the hole in the cardiac wall after the future withdrawal of the pump.

For a better axial fixing of the pump on a cardiac wall with a so-called purse-string suture, a peripheral enlargement 45 may be provided on the housing 10.

FIG. 2 shows the atrial use of the paracardiac blood pump in the right heart support, the housing 10 projecting through the right cardiac auricle 40 of the cardiac wall into the right atrium RA, while the outlet tube 23 is located outside the heart and is connected, via a hose 41, with the pulmonary artery PA conducting the blood from the right ventricle RV into the lung L. The blood returning from the lung L flows through the mitral valve MK into the left ventricle LV. From the left ventricle, the aortic valve AK leads into the aorta AO.

The tricuspidal valve TK is located between the right atrium RA and the right ventricle RV, and the pulmonary valve PK is located between the right atrium RA and the pulmonary artery PA. The superior vena cava OHV and the inferior vena cava UHV lead into the right atrium.

With the blood pump arranged as described above, an essential portion of the length of the housing 10 and the cannula 30 is located in the interior of the heart, while a relatively short portion of the housing projects from the heart, and the outlet tube 23 together with the hose connected therewith lies close against the outside of the heart. Therefore, the blood pump does not occupy substantial room.

The blood pump is implanted into the open heart to effect a heart support for the time of an operation or another intervention. An essential advantage consists in that no heavy-weight and voluminous pumps have to be borne on the thoracic region of the patient.

The pump is so small and light that even the fragile right or left atrium is not substantially deformed by applying and introducing the pump.

In the example illustrated in FIG. 2, the pulmonary valve PK is bridged. Incidentally, the heart continues to beat so that the other heart functions are performed as usual.

FIG. 3 shows the positioning of the pump at the apex 42, i.e., at the tip of the left ventricle LV. Also in this case, the housing 10 is pushed from outside through a puncture hole of the cardiac wall while the outlet tube 23 with a hose 43 connected thereto is connected with the descending aorta AOD. Here as well, the spatially packed arrangement of the pump in a very confined space with as little disturbance as possible can be noticed. The pump delivers from the left ventricle LV into the descending aorta, thereby bridging the aortic valve AK.

In the example of FIG. 4, the housing ten projects from the outside into the left atrium LA, while the outlet tube 23 located outside the heart is connected with the aortic arch AOB or the descending aorta via a hose 44.

It can be noticed that in all cases the positioning of the pump is effected in a space-saving manner, disturbances and impairments of the access to the heart being kept as low as possible.

What is claimed is:

1. A paracardial blood pump, comprising:
   a tubular housing including a longitudinally extending flow channel and a drive unit for an impeller, said drive unit being arranged coaxially therein, and comprising, on the one end, a pump ring with an axial inlet surrounding the impeller and, on the other end, a laterally branching outlet tube; and
   a cannula, arranged in front of said inlet of the pump ring, wherein the housing and the cannula have approximately the same outer diameters of a maximum of 13 mm.

2. The blood pump of claim 1, wherein the inner diameter of the outlet tube is about as large as that of the cannula.

3. The blood pump of claim 1, wherein the pump ring is cylindrical and that a transition region is provided behind the pump ring in flow direction, the diameter of said transition region enlarging from that of the pump ring to that of the flow channel.

4. The blood pump of claim 1, further comprising a pressure sensor for detecting the pressure in the flow channel and wherein a signal from the pressure sensor is evaluated for the detection of different operating states and/or for the detection of the current volume flow.

5. The blood pump of claim 4, wherein the tubular housing has an outside wall and an axial end wall, characterized in that the pressure sensor or a pressure detection opening is arranged on the outside wall or the axial end wall or in the pump ring of the flow channel.

6. The blood pump of claim 1, wherein the cannula projects beyond the pump ring by less than the housing length.

7. The blood pump of claim 1, wherein the flow cross section in the region of the impeller is selected such that the reflux through the pump is less than 1 l/min at a counter pressure of 80 mm Hg when the pump is at a standstill.

8. The blood pump of claim 1, wherein the outlet tube has a cross section enlarging in flow direction.

* * * * *